United States Patent
Bade et al.

(10) Patent No.: US 6,222,056 B1
(45) Date of Patent: Apr. 24, 2001

(54) PROCESS FOR PREPARING VINYLCHLOROSILANES

(75) Inventors: Stefan Bade; Hartwig Rauleder; Uwe Schoen, all of Rheinfelden; Franz-Michael Bollenrath, Marl, all of (DE)

(73) Assignee: Degussa Huels AG, Frankfurt (DE)

( * ) Notice: Subject to any disclaimer, the term of this patent is extended or adjusted under 35 U.S.C. 154(b) by 0 days.

(21) Appl. No.: 09/556,404

(22) Filed: Apr. 24, 2000

(30) Foreign Application Priority Data

Apr. 22, 1999 (DE) .............................................. 199 18 115

(51) Int. Cl.$^7$ ...................................................... C07F 7/14
(52) U.S. Cl. ............................................................... 556/481
(58) Field of Search ............................................... 556/481

(56) References Cited

U.S. PATENT DOCUMENTS

| | | | |
|---|---|---|---|
| 3,666,782 | * | 5/1972 | Mui et al. .............................. 556/481 |
| 5,075,480 | * | 12/1991 | Hange et al. ......................... 556/481 |
| 5,344,950 | * | 9/1994 | Hange et al. ......................... 556/481 |
| 5,808,128 | * | 9/1998 | Fiolitakis ............................. 556/481 |

* cited by examiner

*Primary Examiner*—Paul F. Shaver
(74) *Attorney, Agent, or Firm*—Oblon, Spivak, McClelland, Maier & Neustadt, P.C.

(57) ABSTRACT

The invention relates to a process for preparing vinylchlorosilanes by thermal non-catalyzed reaction of chlorosilanes with vinyl chloride at from 550 to 700° C., using a ring-gap reactor which includes rapidly cooling the hot reaction gases after they have flowed through the ring-gap space, by quenching them with a liquid.

22 Claims, No Drawings

PROCESS FOR PREPARING VINYLCHLOROSILANES

BACKGROUND OF THE INVENTION

1. Field of the Invention

The invention relates to a process for preparing vinylchlorosilanes by non-catalyzed, thermal reaction of chlorosilanes with vinyl chloride using a ring-gap reactor having an, if appropriate, rotating displacement body.

2. Discussion of the Background

Vinyltrichlorosilane is a valuable intermediate, which, owing to its four reactive groups, is suitable for many applications. For example, it is used in the sizing of glass fibers and in the manufacture of cable materials.

DE-C 936 445, DE-A 22 10 189 and, in particular, DE-C 20 02 258 disclose that upon passing vinyl chloride/chlorosilane mixtures and especially vinyl chloride/trichlorosilane mixtures through appropriately heated empty tubes made of ceramic, glass or iron, industrially acceptable yields of vinylchlorosilanes are achieved. The reaction proceeds purely thermally, i.e., without a catalyst. In the reaction of trichlorosilane with vinyl chloride, the following reactions proceed.

Main reaction:

$$C_2H_3Cl + SiHCl_3 \leftrightarrows C_2H_3SiCl_3 + HCl$$

In addition to the above equilibrium reaction, there are the following side reactions and secondary reactions:

$$C_2H_3Cl + SiHCl_3 \rightarrow SiCl_4 + C_2H_4$$

$$4\ SiHCl_3 \rightarrow 3\ SiCl_4 + Si + 2\ H_2$$

$$C_2H_3Cl \rightarrow C_2H_2 + HCl$$

$$C_2H_2 \rightarrow 2\ C + H_2$$

$$C_2H_4 + SiHCl_3 \rightarrow C_2H_5SiCl_3$$

$$C_2H_4 + SiHCl_3 \rightarrow C_2H_3SiCl_3 + H_2$$

$$C_2H_3SiCl_3 + SiHCl_3 \rightarrow Cl_3SiC_2H_4SiCl_3$$

Despite these side and secondary reactions, according to DE 40 01 820 A1, the selectivity for vinyltrichlorosilane, based on the vinyl chloride used in deficient amounts, depending on the ratio of the starting materials and the degree of conversion, is from 50 to 98%, with tubes of from 122 to 150 cm in length and diameters of from 25 to 35 mm, residence times of from 0.2 to 20 seconds, reaction temperatures of from 400 to 750° C. and pressures of from 1 to 3 bar. However, the output (or capacity) of the reactors in this case is only from 0.8 to 3.2 metric tons of vinyltrichlorosilane/month. Selectivity and degree of conversion are inversely proportional to one another; the reactor output passes through a maximum as a function of the degree of conversion. A high selectivity is thus accompanied by an unsatisfactory and economically unacceptable reactor output at a low degree of conversion. According to DE-A 20 02 258, although increasing the size of the tube diameter to 50 mm increases the reactor output in proportion to the greater reactor volume, with still greater diameters, the specific reactor output, based on the reactor volume, decreases. It is therefore impossible to increase the space-time yield of vinyltrichlorosilane, or even only maintain it, by increasing the diameter of the reactor tube to above 50 mm.

An improved process for preparing vinylchlorosilanes by reacting chlorosilanes with vinyl chloride is, according to DE 40 01 820 A1, carried out in a ring-gap reactor which has a treatable reaction tube having an internal diameter $d_1$ in the interior of which is situated an, if appropriate, rotatable cylindrical displacement body which extends over the entire length of the reaction tube, is arranged axially symmetrically and has an outer diameter $d_2$. In this case the relationship $d_1 = d_2 + 2a$ applies, where a is generally at least 1 cm and is always <5 cm. If the displacement body is substantially shorter than the reaction tube, the yield is decreased. This finding corresponds to the teaching of the three abovementioned publications, according to which, in the case of empty tube reactors, the yield falls if the tube diameter exceeds 5 cm. According to DE 40 16 021 A1, the capacity of the reactor, or the space-time yield of the process, can be further increased using a ring-gap reactor if the reaction components are preheated to from 120 to 400° C. prior to entry into the reactor. However, much reactor volume is still lost with this measure, in that the reaction components are heated to approximately 550° C. in order to react further adiabatically in the remaining reactor volume.

SUMMARY OF THE INVENTION

One object of the invention is to increase the space-time yield of vinylchlorosilane.

Another object of the invention is to maintain a high selectivity for the desired vinylchlorosilane at a high degree of conversion.

Another object of the invention is to maintain an economically acceptable high reactor output at a high degree of conversion.

Another object of the invention is to provide a process that allows specific temperature profiles and monitoring of the exiting reaction mixture from the ring-gap reactor.

Another object of the invention is to provide a process in which secondary or minor reactions are suppressed.

Another object of the invention is to provide a process in which the deposition of soot and/or elemental silicon is suppressed.

Another object of the invention is to provide a process in which the formation of undesirable high-boilers is suppressed.

These and other objects have been attained by the present invention, which provides a process for preparing vinylchlorosilanes, that includes:

thermally and non-catalytically reacting chlorosilane with vinyl chloride at a temperature of 550 to 700° C. in a ring-gap reactor to produce a hot reaction gas that comprises vinylchlorosilane, the ring-gap reactor including a ring-gap space; and after the hot reaction gas has flowed through the ring-gap space, rapidly cooling the hot reaction gas by quenching the hot reaction gas with a quenching liquid.

In the novel process, even at high degrees of conversion, a high selectivity for the desired vinylchlorosilane is associated with an economically acceptable high reactor output. This advantageous result is due, inter alloy, to the fact that the process enables specific temperature profile and monitoring after exit of the reaction mixture from the ring-gap reactor. Secondary or minor reactions which, inter alla, can lead to deposition of soot and/or elemental silicon and to the formation of high-boilers are accordingly suppressed.

According to the invention, vinylchlorosilanes and especially vinyltrichlorosilane may be advantageously prepared from trichlorosilane and vinyl chloride. Other suitable chlorosilanes having a substitutable hydrogen atom are, for example, methylhydrogendichlorosilane and ethylhydrogen-dichlorosilane.

BRIEF DESCRIPTION OF THE PREFERRED EMBODIMENTS

Various other objects, features and attendant advantages of the present invention will become more appreciated as the same becomes better understood from the following detailed description.

Preferably, the chlorosilane and vinyl chloride are advantageously used without a diluting liquid or gaseous inert medium and are preferably used in a molar ratio of from 1:1 to 5:1, more preferably from 2:1 to 4:1. The reaction components can be preferably introduced at ambient temperature or, as described in DE 40 16 021 A1, the entire contents of which are hereby incorporated by reference, preheated to from 120 to 400° C., more preferably to from 220 to 400° C., into the ring-gap reactor, where they are further heated. At about 450° C., the exothermic substitution reaction begins which, at about 550° C., achieves a rate such that no further heat supply is necessary; the reaction can therefore essentially proceed adiabatically in the direction toward equilibrium. The zone of the ring-gap reactor in which the adiabatic reaction takes place is therefore not heated. Preferably, the temperatures in this zone are generally in the range from 550 to 700° C., more preferably from 550 to 650° C. Each of the above ranges includes all values and subranges therebetween.

The process according to the invention is preferably carried out at pressures of from 1.1 to 2.0 bar, more preferably from 1.1 to 1.4 bar. The residence times are preferably from 0.2 to 20 seconds, more preferably from 1.0 to 10 seconds. These ranges include all values and subranges therebetween.

As a preferred ring-gap reactor, the reactor described in DE 40 01 820 A1, the entire contents of which are hereby incorporated by reference, can be used. This is preferably vertical and has a treatable cylindrical tube having an equally long, axially symmetrically positioned displacement body which can be arranged to be fixed or can rotate about its longitudinal axis, e.g. at from 10 to 100 rpm, more preferably at from 20 to 40 rpm. Ring-gap reactors for preparing vinylchlorosilanes on an industrial scale can preferably be from 1 to 5 m long, and more preferably from 1.5 to 4.5 m long. The internal diameter of such reactors can preferably be, for example, from 400 to 1200 mm, and more preferably from 500 to 1000 mm. Each of the above ranges includes all values and subranges therebetween.

The inside of the cylindrical tube and the outside of the displacement body form a ring-gap space, in which the starting materials are heated to the starting temperature and the reaction takes place. The displacement body can have a smooth outer wall or can carry on its entire surface, or a part thereof, for example at the entry of the starting material gases, elements which promote the flow velocity and/or the vortexing of the reaction gases and thus keep the ring-gap space free from deposits of solid particles. The elements can be, for example, metal strips which run essentially parallel to the longitudinal axis of the displacement body and have interruptions or are uninterrupted. Alternatively, the continuous or interrupted metal strips can be arranged at any acute angle of from 20 to 50° to the longitudinal axis and then form a guiding spiral. The metal strips can also be mounted as pieces or bumps at regular or irregular intervals on the surface of the displacement body. If a displacement body having a guiding spiral rotates, this preferably takes place in a direction of rotation such that the guiding spiral transports the reaction gases in a direction toward the outlet of the ring-gap reactor. If the metal strips do not form guiding spirals, but are mounted in such a manner that in no case do they transport the reaction gases, the direction of rotation is irrelevant.

Preferably, the displacement body can be cylindrical over the entire length of the reactor. Alternatively, it can be cylindrical from the entry of the starting materials to the starting point of the adiabatic reaction, which, as mentioned, begins at about 550° C., and from this point or from a point situated further toward the outlet of the reactor, can taper abruptly or gradually, e.g. conically or parabolically, if appropriate as far as the diameter of the rotary axle. In this manner, the reactor output or capacity of a plant is increased, the selectivity for the desired vinylchlorosilane, based on reacted vinyl chloride, remaining high. This is surprising, because a substantial part of the reaction takes place in a zone or in a part of the reactor in which the critical parameters <50 mm in diameter (in the process according to DE-A 20 02 258) and <50 mm gap width (in the process according to DE 40 01 820 A1) can be exceeded by far. Depending on the starting materials, the heating power (as described later) and the flow rate, the starting point of the adiabatic reaction is preferably in a region from one to two thirds the length of the reactor, calculated from the entry of the starting materials. Preferably, in the part of the reactor in which the displacement body is no longer cylindrical, no elements promoting the vortexing of the reaction gases are mounted on its surface.

Preferably, the distance between the inner wall of the cylindrical tube and the outer wall of the displacement body in its cylindrical part is at least 10 mm and at most 50 mm, more preferably at least 15 mm and at most 45 mm. Any elements present which promote the vortexing, advantageously project by more than half the gap width into the ring gap. Preferably, the vortex-promoting elements extend over from 60 to 80% of the gap width, more preferably over from 65 to 75% of the gap width. Each of the above ranges includes all values and subranges therebetween.

The cylindrical tube, the displacement body and elements which promote the vortexing of the reaction gases, can be made from most any materials which are stable under the reaction conditions, e.g. of scaling-resistant steels which, in addition to iron, contain as alloy constituents chromium, nickel and titanium and/or molybdenum and/or silicon. Such materials are well-known to one of ordinary skill in the art to which the invention pertains.

Preferably, the ring-gap reactor is provided with a controllable heating apparatus which expediently extends over the entire length of the ring-gap reactor and can be subdivided into a plurality of independent segments. Although it is possible to heat up the starting material gases (including any of chlorosilane, methylhydrogendichlorosilane, trichlorosilane, and ethylhydrogen-dichlorosilane and vinyl chloride) entering into the ring-gap reactor, which are if appropriate preferably preheated to from 120 to 400° C., more preferably to from 220 to 400° C., these ranges including all values and subranges therebetween, so rapidly in the ring-gap reactor that the temperature is about 550° C. and the exothermic reaction proceeds essentially adiabatically without further heat supply as soon as the reaction gases have passed along ⅓ to ⅔ of the reactor length, a heating apparatus in the following part of the reactor also ensures the desired flexibility in the event that the starting point of the adiabatic reaction shifts in the direction toward the exit. The reaction gases are expediently heated indirectly, that is by heat transfer through the wall of the cylindrical tube. For example, the cylindrical tube can be provided with an if appropriate subdivided jacket through which superheated steam or a high-load heat carrier liquid (e.g. a salt melt or liquid metal) can be passed. However, the cylindrical tube is advantageously equipped with an electrical external heater, if appropriate subdivided into segments.

After they have passed through the ring-gap reactor, the hot reaction gases (including any final product(s), side reaction product(s) and/or unreacted starting gases) are rapidly cooled by quenching them with a liquid. The quenching apparatus can be mounted directly beneath the ring-gap reactor and most preferably be no more than about 1.5 m from the ring-gap reactor outlet. A conical quenching vessel consisting of a material resistant under the process conditions is most especially preferred, which vessel is joined by its circular orifice directly to the cylindrical ring-gap reactor. Preferably, the quenching liquid can be injected into the hot reaction gases in a conical shape in the direction of flow, for example by a nozzle or a plurality of nozzles having a preferable diameter of from 8 to 25 rnm, more preferably from 10 to 20 mm. These ranges include all values and subranges therebetween.

A preferred quenching liquid is, for example, trichlorosilane or silicon tetrachloride, the desired vinylchlorosilane, such as vinyltrichlorosilane, or else the crude condensed reaction mixture, which preferably includes from 25 to 50% by weight of the desired vinylchlorosilane. Preferably, the mass flow rate of the quenching liquid is 2 to 6 times the mass flow rate of the gaseous reaction products, and more preferably from 3 to 5 times the mass flow rate of the gaseous reaction products. The evaporating quenching liquid cools the reaction gases, whose temperature at the outlet of the ring-gap reactor is preferably from 550 to 700° C., rapidly to a preferably temperature of <200° C., more preferably to <175° C., most preferably <150° C. so that the equilibrium position virtually no longer changes and unwanted secondary reactions virtually no longer take place. Each of the above ranges includes all values and subranges therebetween. The quenched reaction gases are further cooled and liquefied indirectly. From the liquid phase, the desired vinylchlorosilane is preferably produced by distillation, likewise silicon tetrachloride as byproduct. Unreacted starting materials, trichlorosilane and vinyl chloride, are recycled to the process. The hydrogen chloride can be utilized in another manner, e.g. for preparing chlorosilanes by reacting with silicon.

EXAMPLES

Having generally described this invention, a further understanding can be obtained by reference to certain specific examples, which are provided herein for purposes of illustration only, and are not intended to be limiting unless otherwise specified.

Example 1
Preparation of Vinyltrichlorosilane in a Ring-gap Reactor Using a Quench System The process is carried out in an industrial reactor which is constructed as an electrically treatable ring-gap reactor having a cylindrical outer tube and an axially arranged and likewise cylindrical displacement body having vertically and horizontally arranged metal strips. Reactor and displacement body are 2.5 m long, the internal diameter of the cylindrical outer tube is 600 mm, the outer diameter of the displacement body is 560 mm and the width of the ring gap is accordingly 20 mm. The rotatable displacement body rotates during the experiment at 30 rpm. The ring-gap reactor is followed immediately by a conically tapering quenching vessel having a quenching nozzle arranged in the direction of flow.

A gaseous mixture, preheated to 380° C., of 100 kg/h of vinyl chloride and 700 kg/h of trichlorosilane is fed to the top of the ring-gap reactor. The molar ratio of the two components is 3.23. In the reactor, the starting material gases are further heated until the exothermic reaction begins at about 550° C. The temperature increases to 650° C. The reaction mixture, after a residence time of 1.5 seconds, exits into the quenching vessel at approximately 585° C., to which quenching vessel is fed, as quenching liquid, 2 metric t/h of liquid reaction mixture at a temperature of 30° C. As a result, the temperature of the reaction mixture decreases to 145° C.

At the outlet of the quenching vessel, the reaction mixture, minus the quenching liquid, has the following composition:

| Component | Volumetric flow rate (kg/h) |
| --- | --- |
| Vinyl chloride | 14.9 |
| Trichlorosilane | 495.2 |
| Vinyl trichlorosilane | 193.3 |
| Hydrogen chloride | 43.6 |
| Silicon tetrachloride | 38.1 |
| High-boilers and other minor components | 15.1 |

This gives a vinyl chloride conversion rate of 85% and a vinyl trichlorosilane selectivity, based on reacted vinyl chloride, of 88%. The production output of the reactor is 139 metric t of vinyltrichlorosilane per month.

Example 2—Comparative Example
Preparation of Vinyltrichlorosilane in a Ring-gap Reactor Without a Quench System The reactor of Example 1, but without a quench system, is used. The starting material gases, 100 kg/in of vinyl chloride and 700 kg/in of trichlorosilane (molar ratio 3.23) are again preheated to 380° C. and heated in the reactor to the point that the reaction begins. The displacement body again rotates at 30 rpm. After a residence time of 1.5 seconds, the reaction mixture exits from the ring-gap space at a temperature of 585° C. About 40 cm beneath the displacement body, the temperature is 680° C. The reaction mixture is passed for workup into a system of indirectly cooled product coolers.

The reaction mixture, at the reactor outlet, has the following composition:

| Component | Volumetric flow rate (kg/h) |
| --- | --- |
| Vinyl chloride | 8.9 |
| Trichlorosilane | 486.5 |
| Vinyl trichlorosilane | 176.4 |
| Hydrogen chloride | 39.8 |
| Silicon tetrachloride | 55.2 |
| High-boilers and other minor components | 33.8 |

This gives a vinyl chloride conversion rate of 91% and a vinyltrichlorosilane selectivity, based on reacted vinyl chloride, of 75%. The production output of the reactor is 127 metric t of vinyltrichlorosilane per month.

The comparison with Example 1, in which the reaction mixture is quenched immediately after exit from the ring-gap space, shows a significantly lower vinyltrichlorosilane selectivity at a higher vinyl chloride conversion rate. The lower vinyltrichlorosilane selectivity is caused by a higher proportion of high-boilers and other byproducts as well as a deposition of silicon and soot in the reactor and in the lines to the product coolers. The vinyl chloride conversion rate is above the equilibrium conversion rate, because the high temperatures cause the vinyl chloride to decompose to soot and trichlorosilane to decompose to silicon. These decomposition reactions are exothermic, so that the temperature beneath the displacement body is high and can only be controlled with great difficulty.

It is further recognized that a high vinyl chloride conversion rate alone does not increase the production output of the reactor. The quenching of the reaction gases causes a higher vinyltrichlorosilane selectivity which, despite lower vinyl chloride conversion rate, leads to an increase in reactor output.

This application is based on German application DE 199 18 115.2, filed Apr. 22, 1999, the entire contents of which are hereby incorporated by reference.

Having now fully described this invention, it will be apparent to one of ordinary skill in the art that many changes and modifications can be made thereto without departing from the spirit or scope of the invention as set forth herein.

What is claimed is:

1. A process for preparing vinylchlorosilanes, comprising:
   thermally and non-catalytically reacting a chlorosilane with vinyl chloride at a temperature of 550 to 700° C. in a ring-gap reactor to produce a hot reaction gas that comprises vinylchlorosilane, said ring-gap reactor comprising a ring-gap space; and
   after the hot reaction gas has flowed through the ring-gap space, rapidly cooling the hot reaction gas by quenching the hot reaction gas with a quenching liquid.

2. The process as claimed in claim 1, wherein the ring-gap space comprises a rotatable displacement body which is arranged axially symmetrical in a cylindrical tube and extends over the entire length of the ring-gap reactor.

3. The process as claimed in claim 2, wherein the displacement body comprises over its entire length or a part thereof elements which promote the vortexing of the reaction gases and keep the ring-gap space free from deposits of solid particles.

4. The process as claimed in claim 3, wherein the elements comprise the form a spiral or bumps.

5. The process as claimed in claim 3, wherein the elements have a height of 60 to 80% of the width of the ring-gap space.

6. The process as claimed in claim 2, wherein the displacement body is cylindrical in shape over the entire length of the reactor.

7. The process as claimed in claim 2, wherein the displacement body is cylindrical in shape at a point in the ring-gap reactor wherein a starting material is introduced to a point in the ring-gap reactor wherein an adiabatic reaction begins; and
   wherein from said point in the ring-gap reactor wherein the adiabatic reaction begins or a point in the ring-gap reactor located between the point in the ring-gap reactor wherein the adiabatic reaction begins and a point nearer an outlet of the ring-gap reactor, tapers abruptly or gradually to a diameter greater than or equal to a diameter of a rotary axle for the ring-gap reactor.

8. The process as claimed in claim 1, wherein the ring-gap space has a width of 10 to 50 mm at a point in the ring-gap reactor wherein the displacement body is cylindrical in shape.

9. The process as claimed in claim 8, wherein the width is 20 to 50 mm.

10. The process as claimed in claim 1, wherein said reacting comprises an adiabatic reaction and wherein the temperature of the adiabatic reaction is 550 to 650° C.

11. The process as claimed in claim 1, wherein said reacting is conducted at a pressure of 1.1 bar to 2.0 bar.

12. The process as claimed in claim 1, wherein said reacting is conducted at a pressure of 1.1 bar to 1.4 bar.

13. The process as claimed in claim 1, further comprising a residence time of 0.2 to 20 seconds.

14. The process as claimed in claim 1, further comprising a residence time of 1.0 to 10 seconds.

15. The process as claimed in claim 1, wherein the molar ratio of chlorosilane to vinyl chloride ranges from 1:1 to 5:1.

16. The process as claimed in claim 1, wherein the chlorosilane is trichlorosilane.

17. The process as claimed in claim 1, further comprising preheating the chlorosilane and vinyl chloride either separately or in admixture to a temperature of 120 to 400° C.

18. The process as claimed in claim 1, further comprising preheating the chlorosilane and vinyl chloride either separately or in admixture to a temperature of 220 to 400° C.

19. The process as claimed in claim 1, wherein the quenching liquid comprises at least one selected from the group consisting of trichlorosilane, silicon tetrachloride, vinylchlorosilane, a liquid reaction mixture, and mixtures thereof.

20. The process as claimed in claim 1, wherein a mass flow rate of the quenching liquid is 2 to 6 times the mass flow rate of the reaction gas.

21. The process as claimed in claim 1, wherein said quenching is carried out in a quenching zone that is either directly connected to the ring-gap reactor or is not greater than about 1.5 m from an outlet of the ring-gap reactor.

22. The process as claimed in claim 1, wherein said quenching liquid is injected into the hot reaction gas in a conical shape in the direction of flow by a nozzle or plurality of nozzles having a diameter of 8 to 25 mm.

* * * * *